United States Patent [19]

Miwa et al.

[11] Patent Number: 4,459,853
[45] Date of Patent: Jul. 17, 1984

[54] ULTRASONIC MEASURING SYSTEM

[75] Inventors: Hirohide Miwa, Kawasaki; Hajime Hayashi, Yamato; Takaki Shimura, Machida, all of Japan

[73] Assignee: Fujitsu Limited, Kawasaki, Japan

[21] Appl. No.: 363,852

[22] Filed: Mar. 31, 1982

[30] Foreign Application Priority Data

Mar. 31, 1981 [JP] Japan ................................. 56-48275

[51] Int. Cl.³ ............................................ G01N 29/00
[52] U.S. Cl. ....................................... 73/626; 73/639; 128/660
[58] Field of Search ................. 73/625, 628, 627, 626, 73/639; 128/660

[56] References Cited

U.S. PATENT DOCUMENTS

| 3,156,110 | 11/1964 | Clynes | 73/628 |
| 3,292,018 | 12/1966 | Clynes | 73/628 |
| 3,924,454 | 12/1975 | McElroy et al. | 73/628 |
| 4,161,121 | 7/1979 | Zitelli et al. | 73/626 |
| 4,398,539 | 8/1983 | Proudian | 73/626 |

Primary Examiner—Stephen A. Kreitman
Assistant Examiner—John E. Chapman, Jr.
Attorney, Agent, or Firm—Staas & Halsey

[57] ABSTRACT

A probe is provided which comprises a plurality of ultrasonic transducer elements, and is so arranged as to be capable of simultaneously transmitting and receiving ultrasonic beams of plural frequencies. Means is provided for changing the shapes of the effective acoustic field of the ultrasonic beams of each a predetermined number of frequencies by selectively operating the ultrasonic transducer elements or interchanging transducers. The shapes of the effective acoustic fields of the ultrasonic beams of the plural frequencies are made substantially coincident in accordance with the range of distance from the probe. Thereby, the measuring of the tissue or the like with coincident shaped beams of plural frequencies can be realized.

17 Claims, 20 Drawing Figures

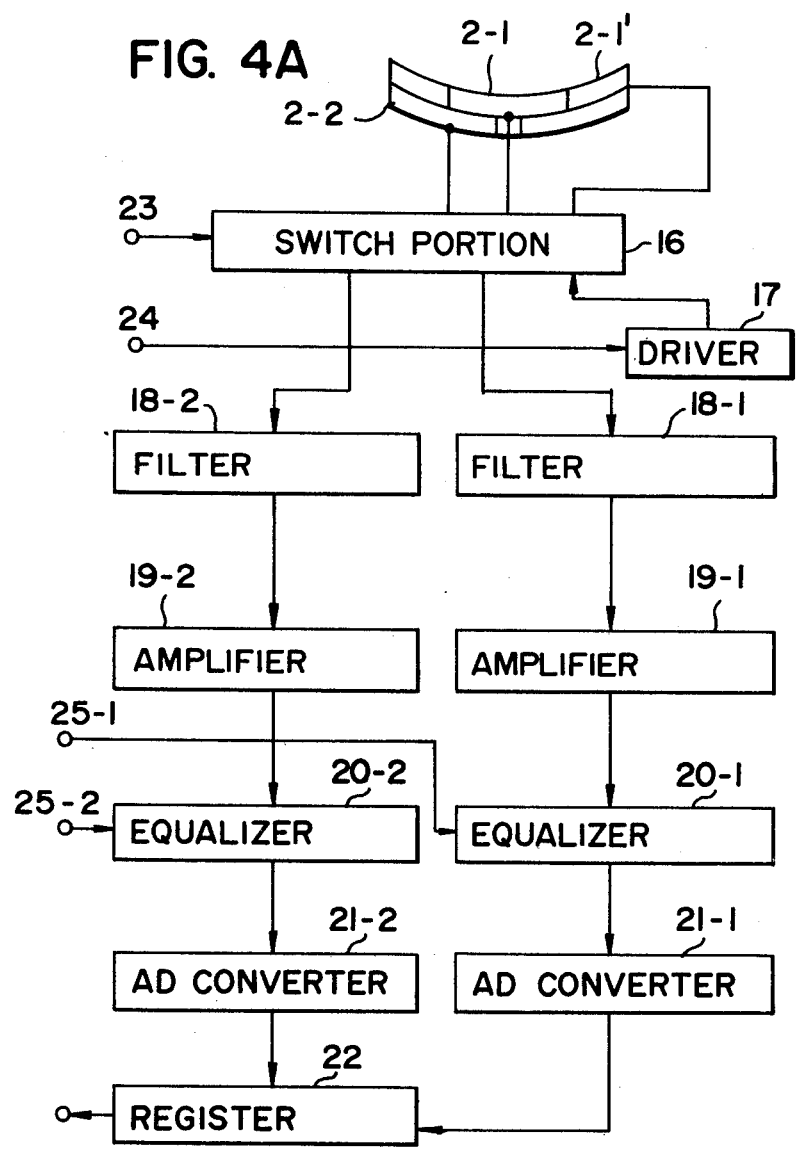

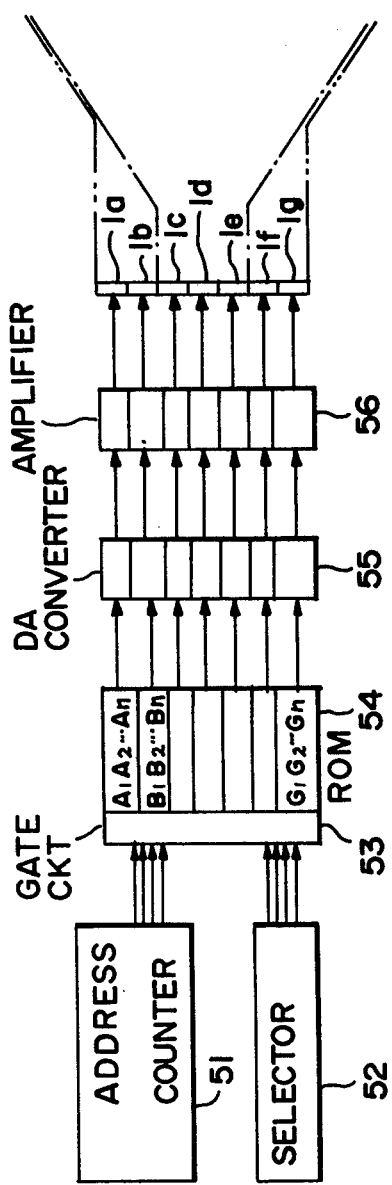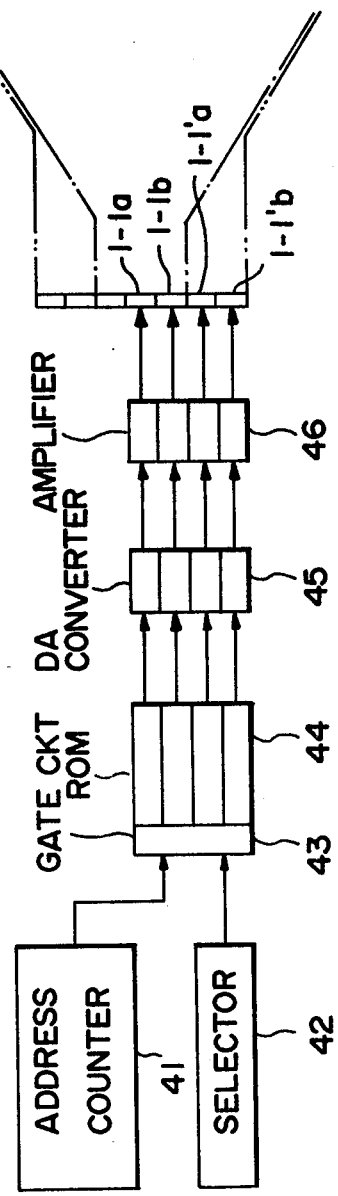

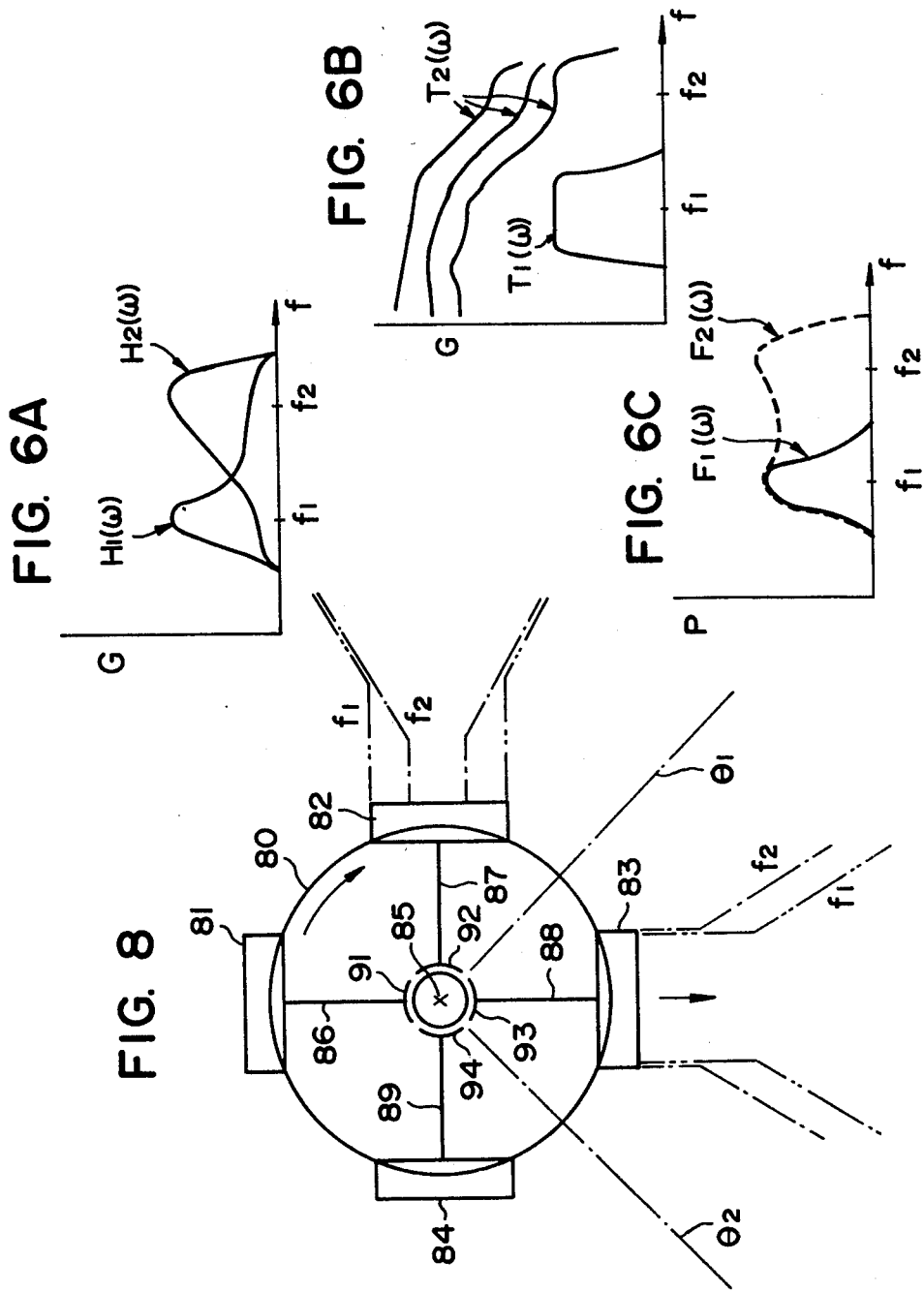

ULTRASONIC MEASURING SYSTEM

BACKGROUND OF THE INVENTION

The present invention relates to an ultrasonic measuring system which applies an ultrasonic wave to a subject of measurement and detects the transmitted or reflected wave from the inside of the subject. More particularly, the invention pertains to an ultrasonic measuring system which carries out measurement by transmitting ultrasonic waves by plural frequencies from an ultrasonic transducer and by controlling the respective effective acoustic fields of the ultrasonic waves to become substantially the same within a certain range of a desired distance from the ultrasonic transducer.

Ultrasonic measuring instruments of the type utilizing transmission, reflection and scattering of ultrasonic waves, such as an ultrasonic camera, a hologram, an echo-imaging device, a computed tomograph, an aperture synthesizer, etc., employ a continuous wave or pulse wave of a predetermined frequency, such as a resonant frequency, or frequency band. An ultrasonic transducer for use in such measuring instruments is constituted by a single ultrasonic transducer element or a plurality of ultrasonic transducer elements, assembled, for instance, in the form of an annular array, a linear scan array, a sector scan array, a discrete aperture synthesizing array or the like. In the latter case, the ultrasonic transducer elements are driven simultaneously or selectively and, in some cases, their timing of transmitting and receiving is varied.

For instance, in the case of a living body being measured, it is known that reflection and attenuation of the ultrasonic wave has a frequency dependency corresponding to the living tissue. Accordingly, by applying ultrasonic waves of plural frequencies to the living body and detecting reflected waves or transmitted waves therefrom corresponding to the frequencies, more information could be obtained than in the case of using ultrasonic waves of a single frequency. In this case, it is necessary that acoustic fields corresponding to the frequencies be of the same shape.

As a transmitted acoustic field from an ultrasonic transducer is substantially dependent on the frequency used and the aperture configuration of the transducer, therefore, the transmitted acoustic field from the transducer differs with frequency when employing ultrasonic waves of plural frequencies.

SUMMARY OF THE INVENTION

It is an object of the present invention to provide an ultrasonic measuring system which carries out measurement by simultaneously transmitting ultrasonic waves of plural frequencies from an ultrasonic transducer and making substantially identical the shapes of the effective acoustic fields of the ultrasonic waves at a desired distance range from the transducer.

Another object of the present invention is to provide an ultrasonic measuring system in which a plurality of ultrasonic transducer elements are selectively driven in accordance with a desired distance range from an ultrasonic transducer to render the shapes of the effective acoustic fields of the ultrasonic waves of plural frequencies substantially identical at the desired distance range.

Yet another object of the present invention is to provide an ultrasonic measuring system in which a plurality of ultrasonic transducer elements are driven by driving waveforms taking into account their frequency dependency to make the shapes of the effective acoustic fields of the ultrasonic waves of plural frequencies to be substantially identical at a desired distance range from the ultrasonic transducer.

Briefly stated, the ultrasonic measuring system of the present invention is provided with a probe made up of a plurality of ultrasonic transducer elements and is adapted for simultaneous transmission or reception of ultrasonic waves of plural frequencies. Means is provided for changing the shapes of the effective acoustic fields of the ultrasonic waves of plural frequencies, and it is controlled so that the effective acoustic fields may assume substantially the same shape.

BRIEF DESCRIPTION OF THE DRAWINGS

FIGS. 4A to 4D are block diagrams of drive circuits embodying the present invention;

FIGS. 6A to 6C show a frequency vs. gain characteristic curves for transducer elements, drive circuits and combined frequency characteristic curves of ultrasonic power;

FIG. 8 is explanatory of the principle of an embodiment using mechanical switching of the shapes of effective acoustic fields.

DETAILED DESCRIPTION OF THE PREFERRED EMBODIMENTS

Figure 1A:
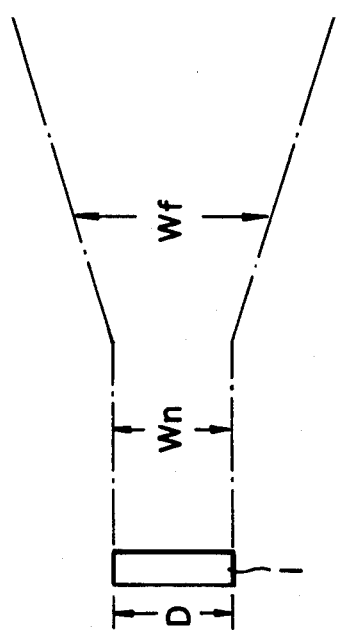
FIG. 1A is explanatory of an ultrasonic beam from a single transducer.

As illustrated in FIG. 1A, the near field of the acoustic field of a disc-shaped ultrasonic transducer 1 having a diameter D which is given by $$Z \leq 1.6(D^2/4\lambda) \tag{1}$$

where $\lambda$ is the wavelength of an ultrasonic wave transmitted from the ultrasonic transducer 1 and Z is the distance therefrom, and the diameter $W_n$ of the ultrasonic beam is given by $$W_n \approx D \tag{2}$$

In the far field given by $$Z > 1.6D^2/4\lambda \tag{3}$$

the diameter $W_f$ of the ultrasonic beam is given by $$W_f = 2.5(\lambda \cdot Z)/D \tag{4}$$

That is to say, the shape of the ultrasonic beam varies with frequency.

The "effective acoustic field" mentioned in this specification is a general term for such acoustic fields as listed below.

(A) Transmitted acoustic field (actual acoustic field)

This is an acoustic field produced by the actually transmitted ultrasonic wave from the transducer, and means an acoustic field actually produced in the subject of measurement by (i) a diverging wave in an acousto-optic camera, hologram or aperture synthesis, (ii) a beam-focused wave from a plane or concave transducer, or (iii) focusing or deflection by timing control of an array element.

(B) Acoustic field to be received (receiving sensitivity field)

This is a field of sensitivity spatial distribution in the case of receiving, by an ultrasonic transducer, an ultrasonic wave transmitted from a certain point in the subject of measurement by virtue of transmission, refraction, reflection or scattering. This field means a receiving sensitivity field produced by (i) the directionality of a transducer, (ii) the dynamic focus in the receiving stage by selection or timing control of transducer elements forming the transducer or (iii) the direction of sensitivity.

(C) Trans-receive acoustic field (field for actually received signal)

This acoustic field to be received is superimposed on the transmitted acoustic field actually produced in the subject of measurement to provide an actually received signal. Accordingly, the trans-receive acoustic field is produced by superimposing, spatially and temporally, the transmitted field and the receiving sensitivity field together. In the case of the reflection method, the same transducer is mostly used both for transmission and reception; in the transmission method, transducers disposed so as to face each other are used for transmission and reception, respectively; and in aperture synthesis, an acousto-optical camera and hologram or, a suitable trans-receive transducer arrangement, is employed. In any case, however, the transmitted acoustic field and the acoustic field to be received are spatially and temporally superimposed on each other to yield an acoustic field of characteristics including transmission and reception. This acoustic field is the trans-receive acoustic field.

(D) Signal processing acoustic field

Sometimes a received signal is subjected to a computing process. For instance, for a focused acoustic field a deconvolution calculation using an inverse spread function, or image processing, is sometimes conducted and, in the aperture synthesis for a diverging acoustic field, the received signal is usually subjected to a computing process. By such processing, the virtual focusing of the actually received signal is steepened or its spatial resolution is raised as if the acoustic field is steepened. The signal processing acoustic field means a virtual acoustic field which is obtained by such processing, or an acoustic field resulting from the processing.

Figure 1B:
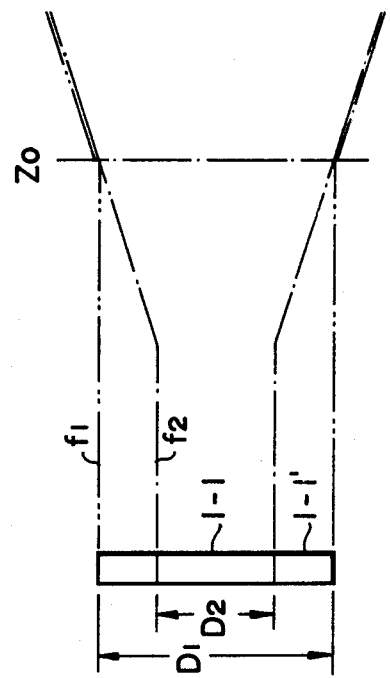
FIG. 1B is explanatory of an example of a probe embodying the present invention and an ultrasonic beam therefrom.

FIG. 1B is explanatory of a probe and an ultrasonic beam in accordance with an embodiment of the present invention. The probe comprises a disc-shaped ultrasonic transducer element 1-1 and an annular ultrasonic transducer element 1-1'. In the case of simultaneously transmitting an ultrasonic wave of a frequency f2 by the disc-shaped ultrasonic transducer element 1-1 of a diameter D2 and an ultrasonic wave of a frequency f1 by both of the annular ultrasonic transducer element 1-1' of a diameter D1 and the disc-shaped transducer element 1-1, by making $D1.f1 = D2.f2$, the shapes of the transmitted ultrasonic beams can be made coincident according to Eqs. (1) to (4) with each other in a far field spaced more than a distance $Z_0$ away from the ultrasonic transducer elements 1-1 and 1-1', as indicated by the one-dot and two-dot chain lines.

Figure 2A:
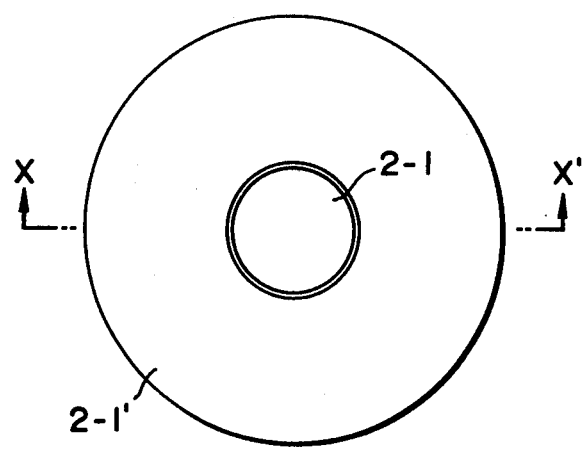
FIGS. 2A and 2B are a front and a sectional view of another example of the probe.
Figure 2B:
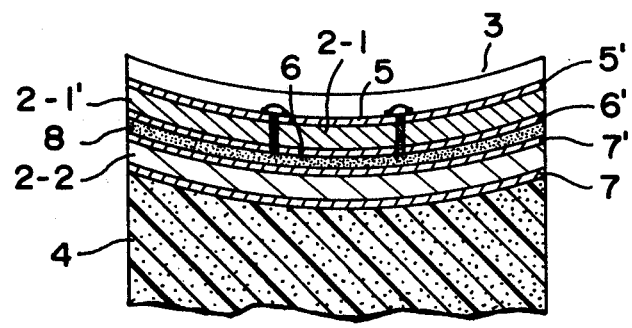

FIGS. 2A and 2B illustrate another example of the probe which comprises three ultrasonic transducer elements, FIG. 2A being a front view of the probe and FIG. 2B a sectional view taken on the line X—X' in FIG. 2A. In FIGS. 2A and 2B, reference numerals 2-1, 2-1' and 2-2 indicate ultrasonic transducer elements made by piezoelectric elements commonly referred to as PZT or PVDF; 3 designates an acoustic impedance matching layer; 4 identifies a backing absorption layer; 5, 5', 6, 6', 7 and 7' denote electrodes; and 8 represents electrically insulating adhesive having a matching function.

The ultrasonic transducer element 2-1 is disc-shaped, the transducer element 2-1' is an annular one disposed outside the transducer element 2-1, and the element 2-2 is a disc-shaped one of substantially the same diameter as that of the transducer element 2-1'. These transducer elements are formed to be concave. The electrodes 5 and 5' of the transducer elements 2-1 and 2-1' are interconnected and grounded. The electrodes 6 and 6' are separated from each other and each has connected thereto a lead wire not shown. Accordingly, the transducer elements 2-1 and 2-1' can be selectively driven by the selective application of a drive signal to the electrodes 6 and 6'. Sandwiched between the electrodes 6, 6' and 7' is the electrically insulating adhesive 8. By applying a drive signal across the electrodes 7 and 7', the transducer element 2-2 is driven.

The human tissue as the subject of measurement has an acoustic impedance of about $1.5[Kg/m^2S]$, a PZT has about $35[Kg/m^2S]$ and a PVDF approximately $4[Kg/m^2S]$. The materials and thicknesses of the acoustic impedance matching layer 3 and the electrically insulating adhesive 8 are selected, and further the acoustic impedances of the front transducer elements 2-1 and 2-1' and the rear transducer element 2-2 are selected, in a manner to assure matching of such acoustic impedances. It is advantageous, for example, to form the front transducer elements 2-1 and 2-1' facing toward the tissue with PVDF elements and the rear transducer element 2-2 with a PZT element. The backing absorption layer 4 absorbs ultrasonic waves emitted backwards and is made, for instance, of a mixture of epoxy resin with tungsten powder.

In the case wherein the transducer elements 2-1 and 2-1' are made of PVDF, and the transducer element 2-2 is made of PZT and ultrasonic waves of center frequencies f1 and f2 (f1 < f2) and band widths $\pm \Delta f1$ and $\pm \Delta f2$, respectively, are to be transmitted, the thickness of the transducer element 2-2 is selected to be ½ of a wavelength $\lambda 1$ corresponding to the frequency f1, and the material and thickness of the electrically insulating adhesive 8 are selected so that ultrasonic waves of a band width ranging from a frequency $(f1 - \Delta f1)$ to $(f1 + \Delta f1)$ may be transmitted from the transducer element 2-2. The effective thickness of the transducer elements 2-1 and 2-1', that is an integrated value of the effects of the acoustic impedance matching layer 3, the transducer elements 2-1 and 2-1' and the electrically insulating adhesive 8, are selected to be ¼ of a wavelength $\lambda 2$ corresponding to the frequency f2, and the material and thickness of the acoustic impedance matching layer 3 overlying the transducer elements 2-1 and 2-1' are selected so that the transducer elements 2-1 and 2-1' may transmit ultrasonic waves of a band width from a frequency (f2−Δf2) to (f2+Δf2). The ratio between the diameter d1 of the transducer element 2-1 and the outer diameter d2 of the transducer element 2-1' is selected as follows:

$$d1/d2 = \lambda 1/\lambda 2 \qquad (4)$$

Figure 3A:
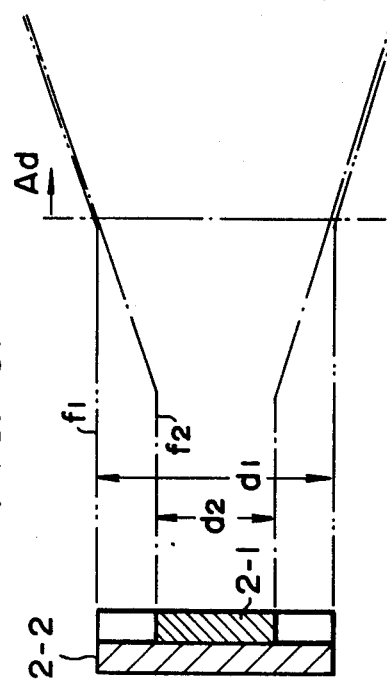
FIGS. 3A and 3B are explanatory of a far and a near field in the case of using the probe shown in FIGS. 2A and 2B.
Figure 3B:
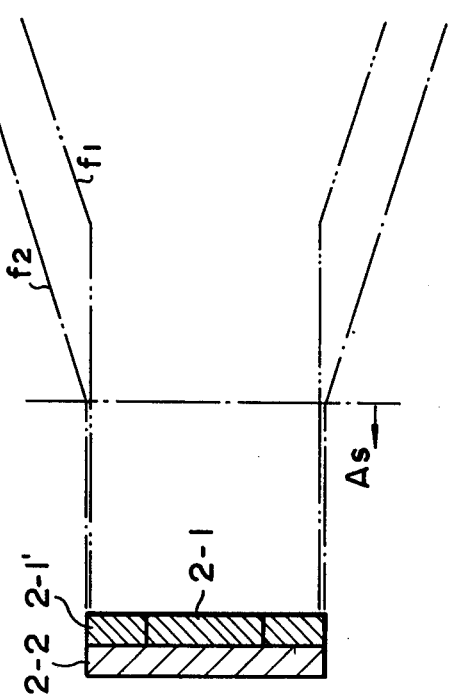

FIGS. 3A and 3B are explanatory of making the shapes of the acoustic fields of the ultrasonic waves coincident with each other through the use of the probe shown in FIGS. 2A and 2B. When the shapes of the far fields Ad coincide with each other, the transducer elements 2-1 and 2-2 are driven in FIG. 3A. That is, ultrasonic waves of the frequencies f2 and f1 are transmitted from the transducer elements 2-1 and 2-2, respectively. By the fulfillment of the condition of Eq. (4), the ultrasonic beams of the frequencies f1 and f2 substantially coincide with each other in the far fields as indicated by the one-dot and two-dot chain lines.

As illustrated in FIG. 3B, when transmitting the ultrasonic wave of the frequency f2 from the transducer elements 2-1 and 2-1' and the ultrasonic wave of the frequency f1 from the ultrasonic transducer element 2-2, the shapes of near fields As coincide with each other since the aperture diameters for emitting the ultrasonic waves of the frequencies f1 and f2 are the same.

As described, by selecting the ultrasonic transducer element 2-1 driven at the frequency f2 in combination with the ultrasonic transducer element 2-2 driven at the frequency f1, the shapes of the far fields can be made substantially the same and, by selecting the ultrasonic transducer elements 2-1 and 2-1', in combination with the transducer element 2-2, the shapes of the near fields can be rendered almost identical with each other.

FIG. 4A illustrates in block form an embodiment of the present invention in which the probe shown in FIGS. 2A and 2B is used both for transmitting and receiving the ultrasonic waves. The transducer elements 2-1, 2-1' and 2-2 are schematically shown for clarity of illustration.

Reference numeral 16 indicates a switch portion; 17 designates a driver; 18-1 and 18-2 identify filters; 19-1 and 19-2 denote amplifiers; 20-1 and 20-2 represent equalizers; 21-1 and 21-2 show AD converters; 22 refers to a register; and 23, 24, 25-1 and 25-2 signify control signal input terminals. The driver 17 operates on a control signal from the input terminal 24 and yields, for instance, an impulse which has a uniform signal component over the working frequency band. The switch portion 16 responds to a control signal from the input terminal 23 to perform switching control, namely for applying the output signal from the driver 17 to all of the transducer elements 2-1, 2-1' and 2-2 or only to the transducer elements 2-1 and 2-2. At the same time, the switch portion 16 operates to supply the filters 18-1 and 18-2 with the signals received by the transducer elements. In consequence, the signal received by the transducer element 2-2 is provided to the filter 18-2 and the signals or signal received by the transducer elements 2-1 and 2-1' or the element 2-1 alone is fed to the filter 18-1. Next, a description will be given of the measuring operation.

(1) Measurement of the near acoustic field

The switch portion 16 operates on the control signal to apply the output signal from the driver 17 to the transducer elements 2-1, 2-1' and 2-2. The transducer elements 2-1 and 2-1' transmit an ultrasonic beam of the center frequency f2 and the transducer element 2-2 transmits an ultrasonic beam of the center frequency f1. Therefore, the shapes of the acoustic fields produced by the ultrasonic waves of the frequencies f1 and f2 coincide with each other in the near field as described previously in respect of FIG. 3B.

Concerning the reflected waves from the near acoustic field in the subject of measurement, the ultrasonic wave of the center frequency f1 is converted by the transducer element 2-2 into an electric signal, and the ultrasonic wave of the center frequency f2 is converted by the transducer elements 2-1 and 2-1' into an electric signal. The former and latter electric signals thus obtained are respectively provided to the filters of the center frequencies f2 and f2 for removal of unnecessary components, thereafter being applied to the amplifiers 19-1 and 19-2, respectively.

The output signals from the amplifiers 19-1 and 19-2 are respectively provided to the equalizers 20-1 and 20-2, wherein they are subjected to correction of the attenuation during transmission in the subject of measurement and so forth, in accordance with control signals from the input terminals 25-1 and 25-2. The equalizer outputs are converted by the AD converters 21-1 and 21-2 into digital signals, which are set in the register 22. The contents of the register 22 are sent to a processor or the like for performing processing such as analysis of the subject of measurement, image display or the like.

(2) Measurement of the far acoustic field

The switch portion 16 operates on the control signal to apply the output signal from the driver 17 to the transducer elements 2-1 and 2-2. In consequence, the transducer element 2-1 transmits the ultrasonic beam of the center frequency f2 and the transducer element 2-2 transmits the ultrasonic beam of the center frequency f1. As described previously with regard to FIG. 3A, the shapes of the acoustic fields by the ultrasonic waves of the frequencies f1 and f2 coincide with each other in the far field. Further, the switch portion 16 operates to supply the filter 18-1 with the signal of the center frequency f2 received by the transducer element 2-1 and the filter 18-2 with the signal of the center frequency f1 received by the transducer element 2-2. The equalizers 20-1 and 20-2 and other devices operate in the same manner as in the case of the measurement of the near acoustic field described above, and measured digital values are set in the register 22. The contents of the register 22 are sent to the processor or the like.

Figure 4B:
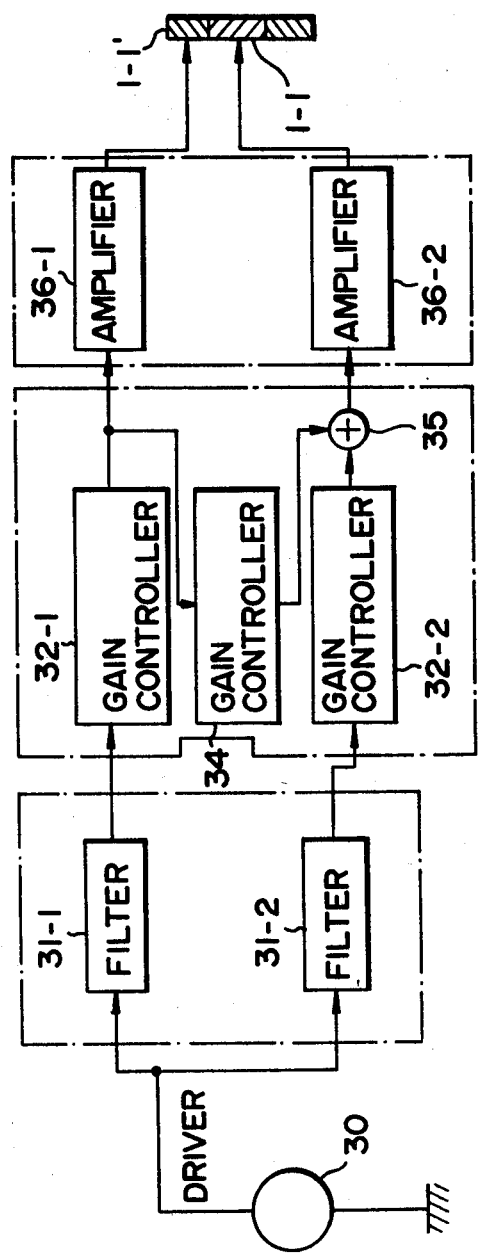

FIGS. 4B, 4C and 4D are block diagrams illustrating the principal parts of the drive circuits in accordance with other embodiments of the present invention. FIG. 4B shows an arrangement for driving the probe described previously in connection with FIG. 1B. The annular ultrasonic transducer element 1-1' is disposed on the outer periphery of the disc-shaped ultrasonic transducer element 1-1. From a driver 30 is yielded a signal having a signal component over a wide band width, which signal is provided to a filter 31-1 of the center frequency f1 and a filter 31-2 of the center frequency f2. The output signals from the filters 31-1 and 31-2 are adjusted by gain controllers 32-1 and 31-2 to a desired magnitude, and the signal of the center frequency f1 is amplified by an amplifier 36-1 and then fed to the transducer element 1-1'.

A portion of the output signal from the gain controller 32-1 is provided via a gain controller 34 to an adder 35, wherein it is added to the output signal from the gain controller 32-2. The adder output is applied to the transducer element 1-1 after being amplified by an amplifier 36-2. Consequently, the transducer element 1-1 is driven by the signals of the center frequencies f1 and f2.

Figure 5B:
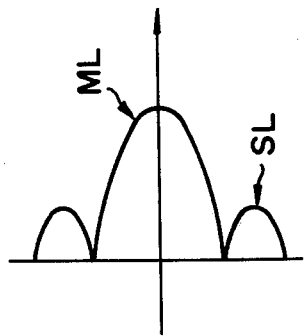
FIGS. 5A to 5D are explanatory of drive signal waveforms, producing a main lobe and a side lobe.
Figure 5D:
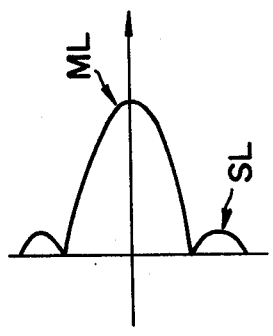
Figure 5A:
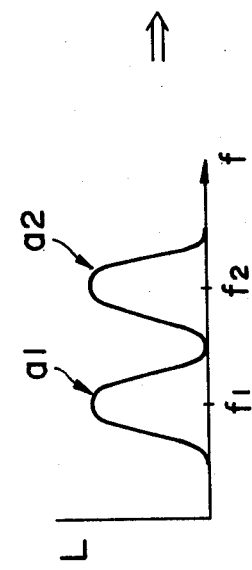
Figure 5C:
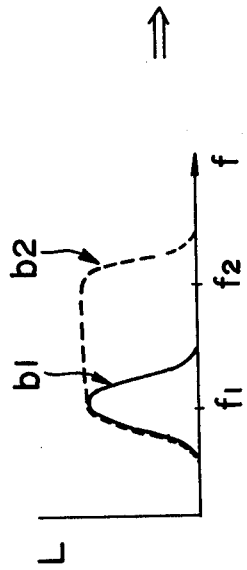

FIGS. 5A and 5C are explanatory of a frequency f and a driving signal level L. As illustrated in FIG. 5A, when applying driving signals a1 and a2 of the center frequencies f1 and f2 to the transducer elements 1-1' and 1-1, respectively, then the shapes of the acoustic fields by the ultrasonic waves of the frequencies f1 and f2 coincide with each other at a position spaced more than the distance $z_0$ apart from the probe as referred to previously in respect of FIG. 1B, but a main lobe ML is accompanied with relatively large side lobes as depicted in FIG. 5B. By applying a signal b1 of the center frequency f1 and a signal b2 including the frequencies f1 and f2 as shown in FIG. 5C to the transducer elements 1-1' and 1-1, respectively, the side lobes SL can be made small relative to the main lobe as illustrated in FIG. 5D.

In FIG. 4B, since a signal including the signals of the center frequencies f1 and f2 can be obtained from the adder 35, the side lobes can be reduced by driving the transducer element 1-1 with the signal b2 shown in FIG. 5C.

In practice, it is difficult to fabricate a transducer which has the same characteristics for the plurality of frequencies f1 and f2. Especially in the case where the center frequencies f1 and f2 are spaced far apart, there usually result such frequency-gain characteristics as indicated by curves $H_1(\omega)$ and $H_2(\omega)$ in FIG. 6A. For instance, the gain G of the transducer element 1-1' of the center frequency f1 has a frequency characteristic such as indicated by the curve $H_1(\omega)$, and the gain G of the transducer element 1-1 of the center frequency f2 has a frequency characteristic such as indicated by the curve $H_2(\omega)$.

Then the frequency-gain characteristic of the drive circuit is controlled as shown in FIG. 6B. That is to say, the gains G of the drive circuit of the transducer elements 1-1' and 1-1 are adjusted to have characteristics as indicated by $T_1(\omega)$ and $T_2(\omega)$, respectively. $T_2(\omega)$ indicates that the gain can be adjusted to have three kinds of characteristics, but it is not limited specifically to them.

By a combination of the frequency-gain characteristics shown in FIGS. 6A and 6B, ultrasonic waves having respective frequency bands, such as illustrated in FIG. 6C, are transmitted. Namely, the powers P of the ultrasonic waves of the frequency characteristics respectively indicated by $F_1(\omega)$ and $F_2(\omega)$ are transmitted from the transducer elements 1-1' and 1-1, by which it is possible to markedly decrease the side lobes and obtain a favorable main lobe configuration.

The frequency-gain characteristic of the drive circuit such as described above can be adjusted by the gain controllers 32-1, 32-2 and 34 in FIG. 4B.

FIG. 4C is a block diagram illustrating an embodiment of the drive circuit for a probe in which the transducer elements 1-1 and 1-1' in FIG. 1B are subdivided into concentric elements 1-1a, 1-1b and 1-1'a, 1-1'b. A memory 44 such as a read only memory or the like has stored therein, corresponding to the individual transducer elements 1-1a, 1-1b, 1-1'a and 1-1'b, data for driving signal waveforms which provide such frequency-gain characteristics as referred to previously in connection with FIGS. 6A, 6B and 6C. Furthermore, the data are selected so that the transducer elements can be driven in a manner to provide higher intensity in the central portion of the ultrasonic beam than in the peripheral portion thereof as in the case of a Gaussian distribution.

An address counter 41 counts clock pulses to generate an address signal of the memory 44, and the address signal is applied via a gate circuit 43 to the memory 44. A selector 42 controls the gate circuit 43 to select the driving signal waveform data stored in the memory 44 and selectively drive the transducer elements. The data sequentially read out from the memory 44 by stepping the address signal are converted by a DA converter 45 into analog signals, which are amplified by an amplifier 46 and fed to the transducer elements 1-1a, 1-1b, 1-1'a and 1-1'b to drive them. For instance, the transducer elements 1-1a and 1-1b are driven by the drive signal including the frequencies f1 and f2, and the elements 1-1'a and 1-1'b are driven by the drive signal of the frequency f1.

FIG. 4D illustrates in block form an embodiment of the drive circuit for a probe formed by a linear array transducer. Ultrasonic transducer elements 1a to 1g are arranged in a line, and data for driving signal waveforms corresponding to the transducer elements are stored in a memory 54. By the application of a sequentially stepping address signal from an address counter 51 via a gate circuit 53 to the memory 54, data ($A_1$, $B_1$, . . . $G_1$) to ($A_n$, $B_n$, . . . $G_n$) corresponding to the individual transducer elements are sequentially read out from the memory 54 and converted by a DA converter 55 into analog signals, which are amplified by an amplifier 56 and then provided to the transducer elements 1a to 1g.

By applying the driving signal including the frequencies f1 and f2 to the transducer elements 1c to 1e and the driving signal of the frequency f1 to the transducer elements 1a, 1b, 1f and 1g, the shapes of the acoustic fields of the ultrasonic waves of the frequencies f1 and f2 can be made to coincide with each other at a predetermined distance from the probe. Moreover, the shapes of the acoustic fields can be changed by selectively driving the transducer elements 1a to 1g under the control of a selector 52. Accordingly, it is also possible to carry out switching between measurement of the near acoustic field and measurement of the far acoustic field as described previously in connection with FIGS. 3A and 3B.

Figure 7A:
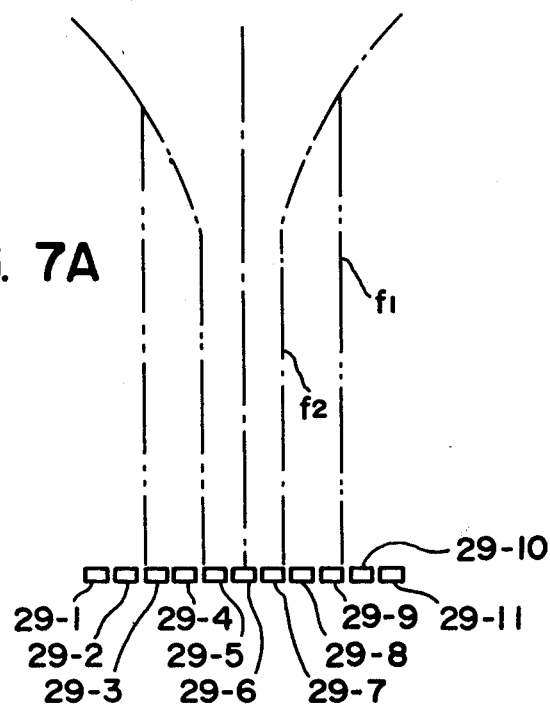
FIG. 7A is explanatory of a linear scan array type probe.

FIG. 7A is explanatory of a linear scan array type probe, in which ultrasonic transducer elements 29-1 to 29-11 are aligned and each element is adapted to be capable of transmitting the ultrasonic wave including the frequencies f1 and f2. In this case, each transducer element can be constructed so that it is able to transmit an ultrasonic wave including the frequencies f1 and f2 by the selection of the driving signal waveform, for example, as in the case of the transducer element 1-1 in FIG. 4B, or by laminating the transducer element 2-2 of the frequency f1 and the transducer elements 2-1 and 2-1' of the frequency f2 as depicted in FIGS. 2A and 2B.

In consequence, during measurement of the near acoustic field the ultrasonic wave including the frequencies f1 and f2 is transmitted from each of the transducers 29-3 to 29-9. During measurement of the far acoustic field the ultrasonic wave of the frequency f1 is transmitted from each of the transducer elements 29-3, 29-4, 29-8 and 29-9 and the ultrasonic wave including the frequencies f1 and f2 is transmitted from each of the transducer elements 29-5 to 29-7, by which the shapes of the far acoustic fields can be made to coincide with each other as indicated by the one-dot and two-dot chain lines.

Figure 7B:
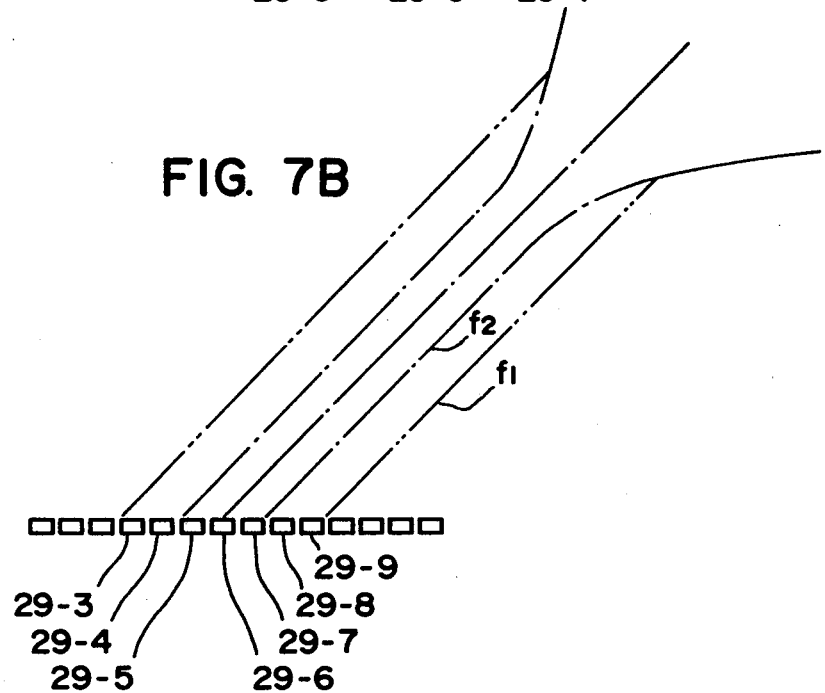
FIG. 7B is explanatory of a sector scan array type probe.

FIG. 7B is explanatory of a sector scan array type probe, in which ultrasonic beams can be directed obliquely on a slant by sequentially displacing the phases of driving signals that are applied to the transducer elements 29-3 to 29-9. Further, the direction of the ultrasonic beam can freely be varied by controlling the phases of the driving signals. Also in this case, it is possible to perform switching between the measurements of the near and far acoustic fields by the selection of the transducer elements which transmit the ultrasonic wave including the frequencies f1 and f2.

FIG. 8 is explanatory of the principle of an arrangement for mechanically switching the shape of the effective acoustic field. On a probe head rotor 80, are fixedly mounted transducers 81 to 84 which transmit ultrasonic waves the acoustic fields of which become uniform at a desired distance, and the probe head rotor 80 is arranged to be rotatable by a shaft 85. Reference numerals 86 and 89 indicate lead wires, and 91 to 94 designate contactors. The contactors 91 to 94 make contact with fixed contacts not shown. For example, when the contactor 93 contacts the fixed contact, the transducer 83 is driven.

In the case where the transducer 82 is designed for the measurement of the far acoustic field and the transducer 83 for the measurement of the near acoustic field, the near acoustic field can be measured when the probe head rotor 80 is held at the illustrated position. When turning the probe head rotor 80 through 90° in the direction of the arrow, the far acoustic field can be measured by the transducer 82 which as an example can be rotated to any position in illustrated angular range between $\theta 1$ and $\theta 2$. In other words, the shapes of the acoustic fields of the ultrasonic waves of the frequencies f1 and f2 can be altered by selectively switching the transducers. Incidentally, the shaft 85 can be driven by an arbitrary drive mechanism such as a motor or the like. The number of the transducers 81 to 84 mounted on the probe rotor head 80 can also be decreased or increased. Moreover, the connection of the transducers 81 to 84 with the stationary part can also be achieved by means of a transformer coupling. The probe head rotor 80 and the transducers 81 to 84 are housed in a vessel filled with oil, jelly or like fluids, so as to prevent the transducers from making direct contact with the subject of measurement when the probe head rotor 80 is turning.

The shape of the effective acoustic field can be changed by such electrical switching means of the selective driving of the ultrasonic transducer elements, the selection of the drive signals and such mechanical switching means as shown in FIG. 8; and it is also possible to employ suitable combinations thereof. Therefore, the near and far acoustic fields can be measured also on a time-shared basis. Further, the number of the frequencies used are not limited specifically to two frequencies but may also be increased. For instance, in FIG. 4C, it is possible to drive the transducer element 1-1$a$ at a frequency between f1 and f2, the element 1-1$b$ at a frequency between f1 and f2' (wherein f2'<f2), the element 1-1'$a$ at a frequency between f1 and f1' (wherein f2'>f1'>f1) and the element 1-1'$b$ at the frequency f1.

Moreover, the present invention is not limited specifically to the two-stage switching between the measurements of the near and far acoustic fields, but it is also possible to adopt an arrangement of multi-stage switching of the range of coincidence, between the shapes of acoustic fields of plural frequencies, by selective driving of the transducer elements. The use of such an arrangement facilitates the analysis of a tissue moving in the body of the subject of measurement.

As has been described in the foregoing, according to the present invention, ultrasonic waves of plural frequencies are simultaneously transmitted and the shapes of acoustic fields of the ultrasonic waves are made to coincide with each other at a desired distance range from a probe; accordingly, the present invention provides for enhanced accuracy in the analysis of a tissue or the like of the subject of measurement which has a frequency dependency.

It will be apparent that many modifications and variations may be effected without departing from the scope of the novel concepts of this invention.

What is claimed is:

1. An ultrasonic measuring system which is provided with a probe and which is operable simultaneously with plural frequencies for measuring the interior of a subject of measurement by respective ultrasonic waves, each said ultrasonic wave having a corresponding effective acoustic field for said measuring, wherein the probe comprises
    a plurality of ultrasonic transducer elements which are capable of simultaneous operation with at least two of said ultrasonic waves of said plural frequencies;
    shape-changing means for changing the shape of the effective acoustic field corresponding to at least one of the ultrasonic waves to substantially coincide to the shape of at least one other of said effective acoustic fields at a desired portion of the interior of the subject at which said measuring is to occur, wherein said desired portion and the respective distance thereof from the probe at which the two respective acoustic fields substantially coincide is selectively changed.

2. An ultrasonic measuring system according to claim 1
    wherein the plurality of ultrasonic transducer elements are disposed adjacent to each other, and
    wherein at least a first one of said ultrasonic transducer elements forms a central portion of the probe, said first ultrasonic transducer element being capable of simultaneous operation with said ultrasonic waves of at least two of said frequencies.

3. An ultrasonic measuring system according to claim 1
    wherein at least two of said plurality of ultrasonic transducer elements are located adjacent each other,
    wherein said two ultrasonic transducer elements are laminated on a third one of said ultrasonic transducer elements, and
    wherein said two ultrasonic transducer elements are operated selectively with at least one of said frequencies while said third ultrasonic transducer element is operated with at least one other frequency.

4. An ultrasonic measuring system according to claim 1 comprising
    said plurality of ultrasonic transducer elements forming a linear array, and means for operating the probe for carrying out at least one of linear and sector scanning.

5. An ultrasonic measuring system according to claim 1 wherein said probe comprises plural sets of said plurality of ultrasonic transducer elements, and the operation of said shape changing means involves operating different ones of said sets of said plurality of ultrasonic transducer elements.

6. An ultrasonic measuring system according to claim 5, wherein each said set is mounted at a respective location on a rotatable probe head rotor, wherein each said set can be selectively operated by rotating said rotor.

7. An ultrasonic measuring system according to claim 1 wherein each of said ultrasonic transducer elements is operated with a driving signal of a level that is adjusted in accordance with the frequency-gain characteristic of the respective transducer element.

8. An ultrasonic measuring system according to claim 7 comprising a memory for storing waveform data for determining said signals in accordance with said frequency-gain characteristics, and means for producing said signals based on the waveform data that is read out from the memory and supplied to the ultrasonic transducer elements.

9. The system of claim 2, comprising an annular ultrasonic transducer element surrounding said first ultrasonic transducer element forming said central portion, wherein said first element is operated with two different ones of said plural frequencies and said annular element is selectively operated with the smaller of said two different frequencies and with said two different frequencies.

10. The system of claim 3, wherein said two elements comprise a central element and an annular element, respectively, said annular element being selectively provided with a respective one of said frequencies that is higher than a respective frequency that is supplied to said third ultrasonic transducer element, and the central element being operated with said higher frequency.

11. The system of claim 1, 2, 3, 9 or 10, comprising means for the operation of said system which includes a filter for each of said plurality of frequencies, and means for selectively connecting said filters respectively to said ultrasonic transducer elements.

12. The system of claim 11, wherein said system is operated so that said ultrasonic transducer elements both transmit and receive said ultrasonic waves with said plurality of frequencies and the substantially coinciding effective acoustic fields.

13. The system of claim 12, comprising means for operating said system so that the side lobes of at least one of the effective acoustic fields corresponding to one of said frequencies are reduced relatively to the respective central lobe.

14. The system of claim 11, comprising means for operating said system so that the side lobes of at least one of the effective acoustic fields corresponding to one of said frequencies are reduced relatively to the respective central lobe.

15. The system of claim 1, 2, 3, 5, 7, 9 or 10 comprising two of said ultrasonic transducer elements operating with respective ones f1 and f2 of said frequencies, and said two transducer elements having respective apertures D1 and D2, wherein the relation of $D1f1 = D2f2$ is satisfied.

16. The system of claim 1, 2, 3, 5, 7, 9 or 10 wherein the respective frequencies of said ultrasonic waves are contained respective frequency bands.

17. The system of claim 16, wherein at least one of said frequency bands include at least two of said plural frequencies.

* * * * *

UNITED STATES PATENT AND TRADEMARK OFFICE
CERTIFICATE OF CORRECTION

PATENT NO. : 4,459,853
DATED : July 17, 1984
INVENTOR(S) : Hirohide Miwa, Hajime Hayashi, Takaki Shimura It is certified that error appears in the above-identified patent and that said Letters Patent is hereby corrected as shown below:

Front Page [57] ABSTRACT
    line 5, "shapes" should be --shape--;
    line 6, delete "each".

Column 2, equation (2), "$W_n \approx D$" should be --$W_n \doteq D$--;
    line 63, "$W_f$ " should be --$W_f$--;
    line 65, "$W_f$ " should be --$W_f$--.

Column 3, line 33, "hologram or," should be --hologram, or-- .

Column 4, line 62, "thickness" should be --thicknesses--.

Column 7, line 15, "$z_0$ should be --$Z_0$--.

Column 9, line 36, after "in" insert --the--.

Column 11, line 21, "characteristics ," should be
    --characteristics,--.
Column 12, line 32, after "contained" insert --in--.

Signed and Sealed this

Third Day of May, 1988

*Attest:*

DONALD J. QUIGG

*Attesting Officer*    *Commissioner of Patents and Trademarks*